(12) United States Patent
Chaloner et al.

(10) Patent No.: US 6,323,370 B1
(45) Date of Patent: Nov. 27, 2001

(54) CATALYTIC PROCESS

(75) Inventors: Penelope Ann Chaloner, West Sussex; Simon Collard, Cambridge; Richard David Ellis, Surrey; Ann Kathleen Keep, Royston, all of (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 09/648,167

(22) Filed: Aug. 25, 2000

(51) Int. Cl.$^7$ .................................................. C07C 209/00
(52) U.S. Cl. ........................ 564/398; 564/446; 564/472; 564/473
(58) Field of Search ................................ 564/446, 472, 564/473, 398

(56) References Cited

U.S. PATENT DOCUMENTS 4,912,260 * 3/1990 Dobson et al. ...................... 564/480

FOREIGN PATENT DOCUMENTS

| 0 022 281 | 1/1981 | (EP) . |
| 0 729 785 | 9/1996 | (EP) . |
| 11 343269 | 12/1999 | (JP) . |
| 95/21151 | 8/1995 | (WO) . |
| 01/05741 | 1/2001 | (WO) . |

OTHER PUBLICATIONS

Bedford, R.B.; Chaloner, P.A.; Dewa, S.Z.; López, G; Hitchcock, P.B.; Momblona, F; and Serrano, J.L., "Anomalous reactivity of triphenylarsine and triarylphosphines of low basicity with [Ir(cod) (py) $_2$] [PF$_6$] and use of the complexes as precatalysts for imine hydrogenation," *Journal of Organometallic Chemistry*, vol. 527, 1997, pp. 75–82.

Bedford, R.B.; Chaloner, P.A.; Claver, C.; Fernandez, E.; Hitchcock, P.B.; and Ruiz, A., "Homogeneous Hydrogenation of Imines Catalyzed by Iridium Complexes," *Dekker*, vol. 62, 1995, pp. 181–188.

Crabtree, R. and Morehouse, S.M., "($\eta^4$—1,5–Cyclooctadiene) (Pyridine)–(Tricyclohexylphosphine) Iridium (I) Hexafluorophosphate," *Transition Metal Organometallic Compounds*, pp. 173–176.

Copy of European Search Report dated Nov. 27, 2000.

\* cited by examiner

*Primary Examiner*—Samuel Barts
(74) *Attorney, Agent, or Firm*—Ratner & Prestia

(57) ABSTRACT

The present invention relates to methods for the reductive amination of a carbonyl-containing compound. $R^1R^2CO$ where $R^1$ and $R^2$ are either H, alkyl, aryl or heterocyclic etc with an amine $NHR^3R^4$ where $R^3$ and $R^4$ arm H, alkyl, aryl, or heterocyclic in the presence of a homogeneous iridium catalyst and gaseous hydrogen.

10 Claims, No Drawings

CATALYTIC PROCESS

The present invention concerns an improved catalytic process. In particular, it concerns a reductive amination process in the presence of a homogeneous iridium catalyst.

Reductive amination is the term used for the process of introducing alkyl groups into ammonia or an amine using an aldehyde or ketone in the presence of a reducing agent. There are large scale reductive amination processes carried out using heterogeneous catalysts, under severe and exacting reaction conditions. These heterogeneous catalysts are used as amongst other reasons it is easy to separate off the catalyst once the reaction is complete. This may be done for instance by filtration. Homogeneous hydrogenation has not generally been used. This is because severe conditions are also require often 50–350° C. and 10–300 atmospheres pressure. It would be desirable to carry out such hydrogenation processes under much milder conditions.

A successful homogeneous reductive amination could lead to an attractive and profitable industrial process. For, example, arylbenzylamines, which can be produced by reacting amines and benzyl halides together, are useful as antioxidants in many synthetic and petroleum lubricants (BK Blandlish et al E.P. 22, 281 (1983) Chem. Abs. 94: 15959b). However, although high yields of arylbenzylamines have been reported, this route is expensive and not environmentally friendly. Also, it is not easy to adapt current methodology to give chiral materials. The production of chiral amines may be of particular importance in the production of pharmaceuticals and agrochemicals.

There are very few homogeneous catalysts for direct reductive amination at the present time, and the development of a method for reductive amination using a homogeneous catalyst could represent a major innovation. This is the problem the present invention sets out to solve. In this regard, the present inventors have found that [Ir(COD)(L)]+, where COD=cyclooctadiene and L=$(R_3P)_2$ or a chelating bisphosphine is a promising homogeneous catalyst for hydrogenation, and more importantly, reductive amination reactions. Certain iridium complex catalysts are known to catalyse imine hydrogenation (J.Organometallic Chem. 527, (1997), 75–82 and Chem. Ind. (Dekker) (1995), 62 (Catalysis of Organic Reactions, 181–8). However these catalysts have not previously been used to catalyse reductive amination reactions.

Accordingly, in the first aspect, the present invention provides a method for the reductive amination of a carbonyl-containing compound $R^1R^2CO$, where $R^1$ and $R^2$ are either H, alkyl, aryl or heterocyclic, or where $R^1$ and $R^2$ together form an aliphatic ring structure, with an amine $NHR^3R^4$ where $R^3$ and $R^4$ are H, alkyl, aryl, or heterocyclic, or $R^3$ and $R^4$ may together form a heterocyclic ring structure, in the presence of a homogeneous iridium catalyst and gaseous hydrogen.

In the second aspect the present invention provides a method for the reductive amination of a carbonyl-containing compound of general formula $R^1R^2CO$, where $R^1$ and $R^2$ are either H, alkyl, aryl or heterocyclic, or where $R^1$ and $R^2$ together form an aliphatic ring structure, with an amine of general formula $NHR^3R^4$ where $R^3$ and $R^4$ are H, alkyl, aryl, or heterocyclic, or $R^3$ and $R^4$ may together form a heterocyclic ring structure, in the presence of a homogeneous iridium catalyst which is attached to a solid support, and gaseous hydrogen.

In one particular embodiment of the invention $R^1$, $R^2$, $R^3$ and $R^4$ may contain further substituents such as alcohol groups, ester groups, or halogen groups.

This synthesis may be achieved through the use of iridium pre-catalysts such as [Ir(diolefin)(L1)(L2)]X where the diolefin may be typically cyclooctadiene or norbornadiene (bicyclo[2.2.1]hepta-2,5-diene) and L1 and L2 are ligands containing a phosphorus donor atom e.g triphenyl phosphine or a heterocyclic nitrogen atom e.g pyridine. Additionally L1 and L2 may be part of the same bidentate ligand e.g. L1+L2=1,2-bis(diphenylphospino)ethane (dppe), The bidentate ligand may be present as a single enantiomer of a chiral compound e.g S,S-(+)-DIOP allowing the process to be used for the synthesis of chiral amines. S,S-(+)-DIOP is (S,S)-(+)-2,3-O-isopropylidene-2,3-dihydroxy-1,4-bis (diphenylphosphino)butane. X is a non-coordinating anion which may typically be a halide or for instance $ClO_2^-$, $BF_4^-$, $PF_6^-$, $BPh_4^-$, $^{RSO}{}_3^-$— or a similar group.

Suitable pre-catalysts for a reaction of this sort are [Ir(COD)(dppb)]$PF_6$, (dppb=1,4-bis(diphenylphosphino) butane), [Ir(COD)(BINAP)]$PF_6$ (BINAP=2,2'-bis (diphenylphosphino)1,1'-binaphthyl), [Ir(COD)(DIOP)]$PF_6$ DIOP=2,3-O isopropylidene-2,3-dihydroxy-1,4-bis (diphenylphosphino)butane).

$Ir(COD)(pyridine)(PCy_3)]PF_6$ ($PCy_3$=tricyclohexylphosphine). These pre-catalysts may be preformed or may be formed in situ, for example by mixing of [{IrCl(COD)}$_2$]+dppb, dppe or BINAP or from [Ir(COD)(pyridine)$_2$]$PF_6$+dppb or dppe.

The reactions of the present invention may be carried out in the presence of a solvent. Suitable solvents include alcohols for instance methanol or ethanol, ethers such as tetrahydrofuran, halogenated solvents for example dichloromethane or 1,2-dichloroethane or hydrocarbons for example toluene. Such solvents may be used in admixture with water.

The reaction is carried out in the presence of gaseous hydrogen at a pressure from 0–10 bar and preferably in the range from 1–5 bar. Moderate temperatures may be used for the reactions of the present invention preferably in the range from 0–150° C. and more preferably in the range from 20–100° C. Even more preferably the reaction may be carried out in the range from 40–70° C. Reaction times will be dependent on the nature of the two main reactants, but will typically be a few hours to a few days and most typically 2–24 hours.

Attachment to a solid support facilitates recovery of the catalyst at the end of the reaction. Suitable methods for the immobilisation of iridium pre-catalysts may include but are not limited to, ionic binding (where the support provides the non-coordinating anion X, and may be typically a hydrocarbon resin in the form of beads or fibres bearing anionic groups such as sulphonate or carboxylate, or an inert support such as zeolite modified with ionic binding material such as poly-oxometallate, e.g polytungstic acid) or covalent binding (where the support provides one or both of the neutral donor ligands L1 or L2, for example as a pendant group bound to a hydrocarbon resin, optionally in the form of beads or fibres.

In a further embodiment of these two aspects of the present invention the iridium pre-catalyst may be isolated prior to use in the reaction or may be generated in situ by reaction of a suitable compound such as [Ir(diolefin)(halide)]$^2$ or [Ir(diolefin)(pyridine)$^2$]X with ligands L. Suitable reaction conditions for the preparation of such compounds will be known to those skilled in the art (see for example Inorg. Synth. vol 24, 173).

Separation or isolation of the product may be carried out by methods known to those skilled in the art and may include filtration, chromatography and so on.

The present invention will now be described by way of the following examples. It will be appreciated that many variations can be made to the invention herein described without departing from the present inventive concept.

EXAMPLES

Examples 1–6 were carried out using the same method. A Schlenk (100 cm$^3$) fitted with a new subaseal was thoroughly purged under both vacuum and nitrogen. The pre-catalyst (in the case that the catalyst is not formed in situ) and the substrate/substrates were placed in the reaction vessel and deoxygenated solvent (10 cm$^3$) was added. Three freeze-pump-thaw cycles were immediately performed under a nitrogen atmosphere, and then a fourth and final freeze-pump-thaw cycle was performed, this time under a hydrogen atmosphere. The solution was allowed to reach room temperature. Vigorous stirring of the solution was then carried out using a magnetic stirrer, and hydrogen was admitted. A slightly over pressure of hydrogen was kept in the reaction vessel during the time of the reaction. The reaction temperature was kept at approx 20° C., unless otherwise stated throughout the reaction, controlled by a water bath. In these reactions, the formation of the product was monitored by gas chromatography and the degree of conversion was defined as the percentage of product relative to total material. Examples 7 and 8 were carried out using a high throughput catalytic screening apparatus.

Example 1

Benzaldehyde (0.404 cm$^3$, 4.0 mmol), di-n-propylamine (0.548 cm$^3$, 4.0 mmol) and [Ir(COD)(dppb)][PF$_6$] (0.070 g, 2 mol %) in dichloromethane were treated as stated above under approx 1 bar H$_2$ at approx. 20° C. for 3 hrs. The yield of N,N-di-n-propylbenzylamine obtained was 39.6%.

Example 2

The same reaction as described above was performed but with dichloroethane as solvent and at a temperature of 60° C. The yield of product obtained was 57.1%

Example 3

Benzaldehyde (0.404 cm$^3$, 4.0 mmol), di-n-propylamine (0.548 cm$^3$, 4.0 mmol) and [Ir(COD)(dppb)][PF$_6$] (0.070 g, 2 mol %) in dichloromethane were treated with 5 µl conc HCl (0.0614 mmol) and then reacted as described in example 1. The yield obtained was 47.2%.

Example 4

Cyclohexanone (0.415 cm$^3$, 4.0 mmol), di-n-propylamine (0.548 cm$^3$, 4.0 mmol) and [Ir(COD)(dppb)][PF$_6$] (0.070 g, 2 mol %) were reacted in dichloromethane at 20° C. for 24 hrs, at approx. 1 bar H$_2$. The yield of N,N-di-n-propylcyclohexylamine obtained was 43.5%.

Example 5

The reaction described above was repeated but with dichloroethane as solvent in place of dichloromethane at 20° C. for 24 hrs. The yield was 76.9%

Example 6

Cinnamaldehyde (0.504 cm$^3$, 4.0 mmol), di-propylamine (0.548 cm$^3$, 4.0 mmol) and [Ir(COD)(dppb)][PF$_6$] (0.070 g, 2 mol %) were treated as stated above, with 1,2-dichloroethane as solvent, and at approx. 1 bar H$_2$ for 3 hours. The yield of product (N,N-di-n-propylcinnamylamine) obtained was 80.9%.

Example 7

Cyclohexanone (0.2 mmol) was reacted with aniline in the presence of the homogenous iridium catalyst formed in situ from [Ir(COD)Cl]$_2$ (0.48 mol %) and BINAP (1.23 mol %). The solvent used was methanol (0.56 ml) acidified with hydrochloric acid (5 µl) ((0.0614 mmol). The mixture was hydrogenated at 2 bar pressure for approximately 20 hours. The yield of product obtained was 70%.

Example 8

Methoxyacetone (0.2 mmol) was reacted with aniline (0.2 mmol) using the catalyst system described in Example 7. The yield of product obtained was 75%.

Example 9

Preparation of N-cyclohexyl Aniline by Reductive Amination
Method A

Cyclohexanone (0.415 cm$^3$, 4.0 mmol), aniline (0.365 cm$^3$, 4.0 mmol), [{Ir(COD)Cl}$_2$] (0.0537 g, 2 mol %) and HCl (5 µl) were treated as stated in the introduction to the examples. Admission of hydrogen was terminated after 20 hours. The solvent used was methanol. The product was purified by column chromatography (SiO$_2$ light petroleum b.p. 80–100° C./ethyl acetate 10:1). Yield=88.6%.
Method B Cyclohexanone (0.415 cm$^3$, 4.0 mmol), aniline (0.365 cm$^3$, 4.0 mmol), [{Ir(COD)Cl}$_2$] (0.0537 g, 2 mol %), triphenylphosphine (0.0420 g, 4 mol %) and HCl (5 µl) were treated as stated above. . The solvent used was methanol. Admission of hydrogen was terminated after 20 hours. The product was purified by column chromatagraphy (SiO$_2$ light petroleum b.p. 80–100° C./ethyl acetate 10:1). Yield=97.6%. The product was characterised by GC-MS and by 1H NMR.

Example 10

Preparation of N-4 diphenyl-2-butylamine by Reductive Amination
Method A 4-phenyl-2-butanone (0.599 cm$^3$, 4.0 mmol), aniline (0.365 cm$^3$, 4.0 mmol, [{Ir(COD)Cl}$_2$] (0.0537 g, 2 mol %), BINAP (0.0498 g, 2 mol %) and HCl (5 µl) were treated as stated above. Admission of hydrogen was terminated after 20 hours. The solvent used was methanol. The product was purified by column chromatography (SiO$_2$ light petroleum b.p. 80–100° C. ethyl acetate 10:1). Yield=98.2%. The product was characterised by GC-MS and 1H NMR.
Method B Trans-4-phenyl-3-buten-2-one (0.585 g, 4.0 mmol), aniline (0.365 cm$^3$, 4.0 mmol), [{Ir(COD)Cl}$_2$] (0.0537 g, 2 mol %), BINAP (0.0498 g, 2 mol %) and HCl (5 µl) were treated as stated in the introduction to the Examples. . The solvent used was methanol. Admission of hydrogen was terminated after 20 hours. Yield=67.2%. The product was characterised by GC-MS and 1H NMR.

Example 11

Preparation of N,4-phenyl-2-butylphenylamine by Reductive Amination

4-Phenyl-2-butanone (0.599 cm$^3$, 4.0 mmol), (R)-(+)-α-methylbenzylamine (0.516 cm$^3$, 4.0 mmol), [{Ir(COD)Cl}$_2$] (0.0537 g, 2 mol %), BINAP (0.0498 g, 2 mol %) and HCl (5 µl) were treated as stated above in the introduction to the Examples. The solvent used was methanol. Admission of hydrogen was terminated after 20 hours. Yield=60.3%. Ratio of diastereoisomers=2:1 (calculated from $^1$H NMR and GLC). The product was characterised by GC-MS and 1H NMR.

What is claimed is:

1. A method for the reductive amination of a carbonyl-containing compound $R^1R^2CO$, where $R^1$ and $R^2$ are either H, alkyl, aryl or heterocyclic, or where $R^1$ and $R^2$ form an aliphatic ring structure with an amine $NHR^3R^4$ where $R^3$ and $R^4$ are H, alkyl, aryl, or heterocyclic, or $R^3$ and $R^4$ may together form a heterocyclic ring structure, in the presence of a homogeneous iridium catalyst and gaseous hydrogen wherein said gaseous hydrogen is at a pressure of approximately 1 to 5 bar.

2. A method for the reductive amination of a carbonyl-containing compound $R^1R^2CO$, where $R^1$ and $R^2$ are either H, alkyl, aryl or heterocyclic, or where $R^1$ and $R^2$ form an aliphatic ring structure, with an amine $NHR^3R^4$ are H, alkyl, aryl, or heterocyclic, or $R^3$ and $R^4$ may together form a heterocyclic ring structure, in the presence of a homogenous iridium catalyst which is attached to a solid support, and gaseous hydrogen wherein said gaseous hydrogen is at a pressure of approximately 1 to 5 bar.

3. A method as claimed in claim 1 or claim 2 where $R^1$, $R^2$ or $R^1R^2CO$ and $R^3$, $R^4$ of $NHR^3R^4$ contain any one or more of the following: alcohol groups, ester groups, halogen groups.

4. A method as claimed in claim 1 or 2 in which the catalyst is either formed in situ or is preformed.

5. A method as claimed in claim 1 or 2 wherein the catalyst may be any one of the following: [Ir(COD)(dppb)]PF$_6$, [Ir(COD)(BINAP)]PF$_6$, [Ir(COD)(DIOP)]PF$_6$, [Ir(COD)(pyridine)(PCy$_3$)]PF$_6$.

6. A method as claimed in claim 1 or 2 wherein the catalyst is formed in situ by reaction of [Ir(COD)Cl]$_2$ or [Ir(COD)(py)$_2$]PF$_6$ with a bisphosphine ligand.

7. A method as claimed in claim 1 or 2 which is performed in the presence of a solvent.

8. A method as claimed in claim 1 or 2 wherein the temperature of the reaction is in the range 0–150° C.

9. A method as claimed in claim 1 or 2 wherein the temperature of the reaction is in the range of 20–100° C.

10. A method as recited in claim 5, wherein the temperature of the reaction is in the range 20–150° C.

* * * * *

UNITED STATES PATENT AND TRADEMARK OFFICE
CERTIFICATE OF CORRECTION

PATENT NO. : 6,323,370 B1
DATED : November 27, 2001
INVENTOR(S) : Chaloner et al.

It is certified that error appears in the above-identified patent and that said Letters Patent is hereby corrected as shown below:

Title page,
After Item "[22] Filed: Aug. 25, 2000" insert the following:
-- [30] Foreign Application Priority Data
    Aug. 27, 1999  [GB]  Great Britain  9920285.5 --.
ABSTRACT,
Line 4, change "arm" to -- are --.

Column 1,
Line 15, change "require" to -- required, --.

Column 2,
Line 15, change "$PF_6^-$, $BPh_4^{-RSO}{}_3$,—" to -- $PF_6^-$, $BPh_4^-$, $RSO_3^-$ --.

Column 4,
Line 50, change "C. ethyl" to -- C/ethyl --.
Line 62, change "N,4-phenyl-2-butylphenylamine" to -- N,4-phenyl-2-butylphenethylamine --.

Signed and Sealed this

Eighth Day of October, 2002

*Attest:*

*Attesting Officer*

JAMES E. ROGAN
*Director of the United States Patent and Trademark Office*